United States Patent [19]

Durham et al.

[11] Patent Number: 4,764,470

[45] Date of Patent: Aug. 16, 1988

[54] ALKALINE PROTEASE PRODUCED BY A BACILLUS

[75] Inventors: Donald R. Durham, Gaithersburg; Edmund J. Stellwag, Damascus; Clyde G. McNamee, Gaithersburg, all of Md.

[73] Assignee: Genex Corporation, Gaithersburg, Md.

[21] Appl. No.: 826,378

[22] Filed: Feb. 5, 1986

[51] Int. Cl.[4] ................. C12N 9/54; C12N 1/20; C12R 1/07

[52] U.S. Cl. .................... 435/221; 435/253; 252/174.12; 252/DIG. 12

[58] Field of Search ............... 435/220–222, 435/253; 252/174.12, DIG. 12

[56] References Cited

U.S. PATENT DOCUMENTS

| | | |
|---|---|---|
| 3,655,513 | 4/1972 | Sternberg . |
| 3,723,250 | 3/1973 | Aunstrup et al. . |
| 3,790,482 | 2/1974 | Jones et al. ................. 252/525 |
| 3,827,938 | 8/1974 | Aunstrup et al. . |
| 3,855,064 | 12/1974 | Vroemen . |
| 3,871,963 | 3/1975 | Tobe et al. . |
| 3,931,034 | 1/1976 | Inamorato et al. . |
| 4,002,572 | 1/1977 | te Nijenhuis ................. 252/99 |
| 4,052,262 | 10/1977 | Horikoshi et al. ............. 435/221 |
| 4,252,663 | 2/1981 | Eriksson . |
| 4,287,101 | 9/1981 | Nishio et al. . |
| 4,429,044 | 1/1984 | Boguslawski et al. . |
| 4,480,037 | 10/1984 | Ichishima et al. ............. 435/221 |
| 4,529,525 | 7/1985 | Dormal et al. . |

FOREIGN PATENT DOCUMENTS

| | | |
|---|---|---|
| 1240058 | 7/1971 | United Kingdom . |
| 1247292 | 9/1971 | United Kingdom . |

OTHER PUBLICATIONS

*Chemical Abstract*, 100:33279j, 1984.
*Chemical Abstract*, 80:144405k, 1974.

*Primary Examiner*—Lionel M. Shapiro
*Attorney, Agent, or Firm*—Saidman, Sterne, Kessler & Goldstein

[57] ABSTRACT

A novel enzyme exhibiting proteolytic activity in alkaline media and stability under alkaline conditions is produced by a novel Bacillus strain designated GX6644 or by its mutants or variants. The enzyme is well-suited for inclusion in washing compositions. A culture of GX6644 has been deposited with the American Type Culture Collection, Rockville, Maryland as ATCC No. 53441.

11 Claims, No Drawings

ALKALINE PROTEASE PRODUCED BY A BACILLUS

TECHNICAL FIELD

The present invention relates to a proteolytic enzyme produced by a novel strain of Bacillus and characterized by activity in alkaline media and at low to moderate temperatures, stability under highly alkaline conditions, and high specific activity. The enzyme is useful in washing compositions.

BACKGROUND OF THE INVENTION

Enzymes having proteolytic activity at alkaline pH are known and have been described in several references, such as U.S. Pat. Nos. 3,674,643 and 4,002,572. Proteolytic enzymes produced by cultivation of members of the genus Bacillus constitute the major source of proteolytic enzymes used in detergent washing compositions. Classified generically as serine proteases, these proteolytic enzymes generally are characterized by sensitivity to diisopropylphosphofluoridate and phenylmethylsulfonyl fluoride (PMSF), resistance to thiol reagents and metal chelators, molecular weights ranging from about 20,000 to about 28,000 daltons, and isoelectric points in the alkaline range. As detergent additives, it is also important for the proper functioning of these enzymes that they be active in solutions at alkaline pH values and in the presence of sequestering agents, surfactants, and in some cases, oxidizing agents.

A basic trend in the detergent market has been for manufacturers to formulate detergents with builder systems other than sodium tripolyphosphate and to provide consumers with products that function at lower wash temperatures. Accordingly, the industry has supplemented their products with enzymes (e.g., proteases and/or amylases) to compensate for detergency reductions. In general, however, proteases formulated into detergents such as Esperase® and Alkalase® from Novo Industries (Bagsuaerd, Denmark), Maxatase® and Maxacal® from Gist-Brocades (Delft, Holland) and Milezyme® from Miles Laboratories (Elkhark, IN) have temperature optima at about 60° C. The enzyme of this invention has a temperature optimum between 45°–50° C. and therefore is more suited for warm (30°–40° C.) or cold (15°–30° C.) temperature washings. Furthermore, as shown below, the protease of this invention exhibits a significantly higher specific activity at 40° C. using casein as substrate as compared to several enzymes on the market.

Accordingly, it is an object of the invention to provide an enzyme which is highly active on proteinaceous material at high pH and moderate temperatures. It is also an object of the present invention to provide a novel proteolytic enzyme which exhibits good stability under alkaline conditions.

It is an additional object of this invention to provide a process for preparation of such an alkaline proteolytic enzyme.

Other objects and advantages of the invention will become apparent from the following detailed description.

SUMMARY OF THE INVENTION

In accordance with the present invention, there is disclosed a novel Bacillus species which produces a novel proteolytic enzyme. The enzyme is characterized as novel due to its amino acid composition and its immunological properties. Furthermore, the enzyme exhibits a high specific activity in comparison to several enzymes described in the art. The enzyme can be produced by cultivating a novel Bacillus strain, designated GX6644, in a nutrient medium and recovering the proteases therefrom.

The protease produced by Bacillus strain GX6644 is useful in detergent compositions.

DETAILED DESCRIPTION OF THE INVENTION

The present invention is directed to a novel enzyme possessing proteolytic activity under alkaline conditions. The enzyme is produced by cultivating a novel alkalophilic Bacillus species, designated GX6644, under suitable conditions. The protease is useful as an additive to heavy-duty liquid and solid detergents. As will be illustrated below, the enzyme produced by Bacillus strain GX6644 is characterized by: its stability under alkaline conditions, activity over a broad pH range, and high activity at low to moderate temperatures. A culture of Bacillus GX6644 has been deposited with the American Type Culture Collection, Rockville, MD, and been given accession number ATCC No. 53441.

The novel Bacillus species which produces the proteases of this invention was isolated from an alkaline soil sample taken in Maryland by means of a specific isolation procedure. The isolation was conducted at a pH within the alkaline range and at a temperature of 30°–37° C.

To obtain the enzyme of interest, the organism is cultivated under aerobic conditions in an alkaline nutrient medium containing an assimilable source of nitrogen, carbon and trace elements, and the proteolytic enzyme is recovered from the fermentation broth.

A variety of growth media can be used for cultivating Bacillus GX6644. To obtain the enzyme an aqueous fermentation medium may contain 0.1 to 1.0% yeast extract, 0.1 to 1.0% peptone, 0.1 to 0.2% inorganic phosphorous, and an assimilable carbon and energy source such as glucose, starch, or dextrins. Furthermore, certain amounts of various metal salts, such as calcium and magnesium, as well as several trace elements preferably are added.

A vigorous aeration is generally maintained during the fermentation and the pH of the medium suitably is kept between about 8.0 and about 10.5, and preferably between 9 and 10. The fermentation temperature is suitably in the range of about 30° C. and 40° C., and preferably is about 37° C. A productive fermentation typically is about 12 to about 30 hours in length and preferably is within the range of about 14 to 25 hours.

The enzyme can be recovered from the fermentation medium in accordance with conventional procedures. The medium first is centrifuged to remove cellular materials, then the enzyme can be precipitated by adding inorganic salts, such as ammonium sulfate, or an organic solvent, such acetone, to the supernatant, and the enzymes then can be separated by ion-exchange chromatography methods (see Example 2). The characteristics of the protease from GX6644 are described in detail below.

The GX6644 protease can be formulated into washing compositions. To date, a drawback in using enzymes in washing compositions has been that the enzymes have not been stable in an alkaline pH environment; consequently the pH of the washing compositions typically has been limited. This is disadvantageous, for the cleaning abilities of washing compositions increase as the pH becomes more alkaline. The GX6644 protease provides a means for overcoming this problem, for, as shown below, it is stable under alkaline conditions.

The protease of this invention may be formulated into washing compositions in accordance with conventional procedures. The GX6644 protease is added to the composition in an amount sufficient to give the final composition a proteolytic activity of about 1,000 to about 8,000 DU/g, and preferably about 2,000 to about 4,000 DU/g. DU stands for Delft Units, and refers to a method for the determination of enzyme activity described in British Pat. No. 1,353,317.

The washing compositions to which the GX6644 protease is added comprise a detergent and, optionally, a detergent builder, fragrance, foam booster and coloring agent. Useful detergents include those detergents conventionally included in washing compositions, including anionic surface active agents, such as, for example, alpha-olefin sulfonates, and nonionic surface active agents, such as ethoxylated alcohols. One detergent or a mixture of detergents may be included in the composition, typically in an amount ranging from about 5 to about 20 percent by weight of the final composition. Any of the optional ingredients, if desired, may be added in conventional amounts. A useful detergent builder is nitriloacetic acid.

PROPERTIES OF GX6644 PROTEASE

A. Temperature/Activity Relationship

For determining protease activity, the Delft method was used as described in British Pat. No. 1,353,317, except in most cases 0.4% $Na_5P_3O_{10}$ (STPP) was used as a buffer with the pH adjusted to 10.0. Thus, Delft units are expressed as alkaline Delft units (ADU). Protease activity, in some cases, was determined by measuring peptidase activity. The increase in absorbance at 410 nm due to the release of p-nitroaniline from succinyl-L-alanyl-L-alanyl-L-prolyl-L-phenylalanyl-p-nitroanilide (sAAPFpN) was monitored spectrophotometrically (Del Mar, E. G., et al., Anal. Biochem. 99:316 [1979]). The reaction mixtures contained in a final volume of 0.7 ml, 0.001M sAAPFpN, 0.1M CAPS [3-(cyclohexylamino) propane sulfonic acid] buffer, pH 10.5 and a suitable amount of enzyme. The temperature optimum for GX6644 protease was determined by the Delft method at pH 10.0 and pH 8.5. At pH 10.0 and pH 8.5, GX6644 protease had optimal activity at 45°–50° C.

|  | % Relative Activity | |
| --- | --- | --- |
| Temperature | pH 8.5 | pH 10.0 |
| 20 | 17 | 21 |
| 25 | 23 | 36 |
| 30 | 33 | 40 |
| 35 | 52 | 61 |
| 40 | 62 | 74 |
| 45 | 88 | 100 |
| 50 | 100 | 100 |
| 55 | 65 | 36 |
| 60 | 38 | 21 |

B. pH/Activity Relationship

For the determination of the pH/activity profile, the Delft assay was modified to the pH at which the activity was determined. The final pH of each reaction mixture was recorded with a Beckman pHI 40 pH meter, equipped with a thermocompensator, calibrated at 40° C.

The enzyme exhibits the following pH/activity profile:

| Measured pH | 7.2 | 8.1 | 8.5 | 9 | 9.5 | 10 | 10.4 | 11 | 11.4 | 12 |
| --- | --- | --- | --- | --- | --- | --- | --- | --- | --- | --- |
| Relative Activity (%) | 37 | 48 | 53 | 59 | 61 | 74 | 88 | 100 | 93 | 45 |

C. Molecular Weight and Isoelectric Point

The molecular weight and isoelectric point of the protease from GX6644 were determined and compared to published values for several known proteases: (1) subtilisin Carlsberg, described in Delange and Smith, J. Biol. Chem., 243:2134 (1968); (2) the enzyme from Bacillus strain PB92, described in U.S. Pat. No. Re.30,602; (3) the enzyme from Bacillus sp. 221 described in U.S. Pat. No. 4,052,262; (4) the enzyme from Bacillus firmus, described in Dutch Patent Application No. 72.07050; (5) the enzyme from Bacillus sacchariticus, described in U.S. Pat. No. 3,622,458 and (6) the enzyme from Bacillus sp. NSK-21 described in U.S. Pat. No. 4,480,037. A comparison of these enzymes is depicted in the following table:

|  | 1 | 2 | 3 | 4 | 5 | 6 | GX6644 |
| --- | --- | --- | --- | --- | --- | --- | --- |
| Molecular Weight | 27,3000 | 25,5000 | 30,000 | 26,000 | 22,700 | 22,000 | 26,500 |
| Isoelectric Point | 9.3 | 10.5 | 9.4 | 11.0 | 9.3 | 7.4 | >9.5 |

D. Amino Acid Composition and $NH_2$-Terminus

The $NH_2$-terminal amino acid of the protease from GX6644 was determined as glutamine. By contrast, alanine is the $NH_2$-terminus of the protease subtilisin Carlsberg (Delange and Smith, J. Biol. Chem., 243:2134 [1968]), and the proteases from Bacillus sp. 221 (U.S. Pat. No. 4,052,262), B. subtilis (Tsuru, et al., J. Agric. Biol. Chem. 31:330 [1967]) and subtilisn BPN' from Bacillus amyloliquefaciens (Matsubara, et al., J. Biol. Chem. 240:1125 [1965]).

The amino acid composition of GX6644 protease was determined and compared to several other proteases: (1) subtilisin Carlsberg (Delange and Smith, J. Biol. Chem., 243:2134 [1968]); (2) subtilisin BPN' (Matsubara et al., J.

Biol. Chem. 240:1125 [1965]); (3) the enzyme (component A) from Bacillus sp. PB92 (U.S. Pat. Re. 30,602); (4) the enzyme from Bacillus sp. 221 (U.S. Pat. No. 4,052,262); (5) the enzyme from *Bacillus sacchariticus* (U.S. Pat. No. 3,622,458); (6) the enzyme from *Bacillus firmus* (Dutch Patent Application No. 72,07050 and (7) the enzyme from Bacillus sp NSK-21 described in U.S. Pat. No. 4,480,037. The composition of the GX6644 protease as compared to these proteases is shown in the following table:

| amino acid | 1 | 2 | 3 | 4 | 5 | 6 | 7 | GX6644 |
|---|---|---|---|---|---|---|---|---|
| LYS | 9 | 11 | 6 | 6 | 6 | 4 | 4 | 4 |
| HIS | 5 | 6 | 7 | 8 | 5 | 6 | 8 | 5 |
| ARG | 4 | 2 | 9 | 8 | 3 | 6 | 8 | 8 |
| ASP | 28 | 28 | 27 | 29 | 20 | 23 | 27 | 31 |
| THR | 19 | 13 | 16 | 18 | 14 | 14 | 10 | 13 |
| SER | 32 | 37 | 30 | 23 | 37 | 22 | 17 | 16 |
| GLU | 12 | 15 | 15 | 16 | 12 | 14 | 14 | 15 |
| PRO | 9 | 14 | 12 | 16 | 10 | 12 | 7 | 9 |
| GLY | 36 | 33 | 31 | 39 | 25 | 30 | 30 | 39 |
| ALA | 42 | 37 | 36 | 45 | 27 | 32 | 26 | 39 |
| CYS | 0 | 0 | 0 | 0 | 0 | 0 | 0 | 0 |
| VAL | 31 | 30 | 22 | 27 | 20 | 21 | 20 | 26 |
| MET | 5 | 5 | 3 | 4 | 3 | 2 | 4 | 5 |
| ILE | 10 | 13 | 8 | 9 | 12 | 7 | 10 | 11 |
| LEU | 16 | 15 | 18 | 22 | 12 | 16 | 14 | 13 |
| TYR | 13 | 10 | 7 | 7 | 9 | 6 | 12 | 4 |
| PHE | 4 | 3 | 2 | 2 | 2 | 2 | 4 | 5 |
| TRP | 1 | 3 | 3 | 5 | 3 | N.D. | 0 | N.D. |
| SΔQ | 486 | 665 | 384 | 282 | 875 | 318 | 394 | 0 |

A measure of compositional relatedness (SΔQ), as shown in the table above, is the sum of the square of the difference in mole fractions of each amino acid that can be readily and quantitatively determined in a protein hydrolysate. In over 5,000 pairwise comparisons of amino acid compositions, Marchalonis and Weltman (*Comp. Biochem. Physiol.* 38:609 [1971]) demonstrated that discernible similarities of amino acid sequence were found in 98% of protein pairs with an SΔQ of less than 100. Based on this method of comparison, the degree of homology betwen the GX6644 protease and other proteases is low.

E. Immunological Cross-Reactivity

Antisera to the protease from GX6644 and subtilisin BPN' were prepared and diffused against PMSF-inactivated proteases on Ouchterlony double-diffusion gels to assess cross-reactivity. Antiserum prepared against the protease from GX6644 was diffused against subtilisin Carlsber9 (Delange and Smith, *J. Biol. Chem* 243: 2134 [1968]); subtilisin BPN' (Matsubara et al., *J. Biol. Chem.* 240:1125 [1965]) and a protease purified from a commercial source, Enzeco ® (Enzyme Development, Division of Biddle Sawyer Corporation, N.Y., N.Y.; the Enzeco ® sample was purified by conventional cation-exchange chromatography). The antiserum directed against the GX6644 protease reacted with the GX6644 protease forming a precipitin band but not with the other proteases. Antisera directed against subtilisin BPN' did not cross-react with the GX6644 protease.

F. Specific Activity

The specific activity of GX6644 protease was determined using the Delft method in 0.4% STPP (pH 10.0). The specific activity of GX6644 protease was compared to purified preparations of subtilisin Carlsberg (Delange and Smith, *J. Biol. Chem.* 243:2134 [1968]); subtilisin BPN' (Matsubara et al., J. Biol. Chem. 240:1125 [1965]), and Enzeco ® (purified as described in E):

| Enzyme | ADU/mg Protein |
|---|---|
| GX6644 | 7,355 |
| Subtilisin Carlsberg | 5,239 |
| Subtilisin BPN' | 3,445 |
| Enzeco ® | 4,496 |

Taxonomy of GX6644

For the taxonomic determination, use has been made of Gordon et al. ["The Genus Bacillus," U.S. Dept. of Agric. Handbook No. 427 (1973)]. The sporulation of Bacillus GX6644 was induced by cultivating cryogenically preserved cultures on potato starch carbonate medium (PSCM) agar.

Cell Morphology a. Vegetative cells: (motile) rods, equatorially swollen, singular in general, but also occurring in chains of 3 to 4 in length.
b. Sporangia: no swelling.
c. Spores: 0.3–0.4 by 0.6–0.8; circular; optically refractile under phase contrast; fail to swell the sporangium

Further Characteristics a. Growth temperatures:
  Maximum 45°–50° C.
  Minimum 12°–20° C.
b. Gram reaction: Positive
c. Growth on solid agar media: no growth occurs on nutrient agar buffered at pH 7.0. There is good growth on nutrient agar buffered at pH 7.0 supplemented with 2% NaCl and excellent growth and sporulation on nutrient agar buffered at pH 9.5 to 10.0. Growth occurred on nutrient agar supplemented with 7.5% NaCl at pH 10.0.
d. Colony morphology: Colonies formed on PSCM agar are mustard yellow, raised, with an entire edge.
e. Biochemical reactions: No formation of a pigment on tyrosine or glucose agar at pH 10.0. Positive starch hydrolysis on potato starch agar at pH 10.0. Strong liquefaction of gelatin on gelatin/nutrient agar at pH 10.0. Clear casein digestion on milk agar at pH 10.0. Strain is catalase-positive.

The invention disclosed and claimed herein is further illustrated by the following examples which are presented for illustrative purposes only and are not to be construed as limiting.

EXAMPLE 1

The fermentation of Bacillus GX6644 was accomplished in a medium containing 10 g/l Bactopeptone, 10 g/l Bacto-yeast extract, 20 g/l soluble potato starch, 1 g/l $K_2HPC_4$ and trace elements. The medium composition without trace elements was sterilized at a temperature of 120° C. and 15 p.s.i. for 30 minutes. After cooling, 7.1 ml of trace elements were added per liter. Trace elements were made as four separate solutions:

1. 5.4 g $FeCl_3.6H_2O$, 1.44 g $ZnSO_4.7H_2O$, 1.0 g $MnCl_2.4H_2O$, 0.25 g $CuSo_4.5H_2O$, 0.25 g $CoSO_4.6H_2O$, 0.062 g $H_3BO_3$, 13.3 ml concentrated HCl to 1 liter distilled water;
2. 61.6 g $MgSO_4.7H_2O$, 44.8 ml concentrated HCl to 1 liter distilled water;
3. 24.1 g $NaMoO_4.2H_2O$ to 1 liter distilled water, and;

4. 100 g CaCl$_2$.2H$_2$O to 1 liter distilled water.

Solutions 1, 2, 3 and 4 were mixed at a ratio of 5:1:0.1:1 before addition to the composition. The final pH was adjusted to 9.5 by the addition of 20% (weight/volume) Na$_2$CO$_3$. The inoculation culture was prepared by inoculating the medium described above with Bacillus GX6644 and incubating at 37° C. for 18 hours on a shaking apparatus adjusted to 300 rpm.

The fermentation medium was inoculated with 1% volume of the inoculation culture. The fermentation was performed at 37° C. in a stirred tank fermentor equipped with a pH controlling device and a dissolved oxygen concentration measuring device. Cell growth was monitored by periodically removing samples and measuring optical density at 660 nm. Protease activity was measured spectrophotometrically using sAAPFpN as substrate and by the Delft method. Fermentation was continued for 12–15 hours. During this period, Bacillus GX6644 produced 22,000 peptide units of protease per liter or $6 \times 10^6$ ADU per liter.

EXAMPLE 2

The proteolytic enzyme produced by Bacillus GX6644 was purified by cation-exchange chromatography. The enzyme produced in Example 1 was recovered from the fermentation broth following centrifugation to remove cellular materials. The enzyme in the supernatant fraction was concentrated by adding three volumes of ice-cold acetone at 4° C. The solution was equilibrated for 60 minutes, then centrifuged at 12000×g at 4° C. for 2 hours. The pellet was resuspended in ice-cold deionized water and dialyzed against three, 3-liter changes at 4° C., then two times against 0.02M potassium phosphate buffer, pH 6.0. Forty grams (wet weight) of sulphoxethyl-cellulose SE53 (Whatman, Ltd, Maidstone, Kent) were equilibrated with five volumes of 0.4 mM potassium phosphate buffer (pH 6.0) for two hours. The cellulose then was washed with 0.02M potassium phosphate buffer (pH 6.0). The SE53 cellulose was added to a chromatography column. The dialyzed extract was loaded onto the column at a rate of two milliliters per minute; ninety-seven per cent of the proteolytic activity was retained. The column was washed with 300 milliliters (6 bed volumes) of phosphate buffer at a flow rate of 0.25 ml per minute. GX6644 protease was eluted with a linear gradient of 0–0.5M NaCl in a final volume of 500 milliliters of 0.02M potassium phosphate buffer (pH 6.0) at a flow rate of 1 milliliter per minute; 10 milliliter fractions were collected and protease activity was determined. The protease from GX6644 eluted between 0.125–0.2M NaCl with peak activity eluting at 0.16M NaCl.

Fraction containing protease activity were pooled and concentrated by acetone precipitation.

EXAMPLE 3

For stability studies under alkaline conditions, the protease from Bacillus GX6644 was recovered from a fermentation broth as before (Example 1) and concentrated at 4° C. by the addition of ammonium sulfate (582 g/l). The protease was precipitated from the ammonium sulfate solution by centrifugation at 22,000×g for 20 minutes at 4° C. The pelleted protein was resuspended in ice-cold deionized water and dialyzed against three, 4-liter volumes of deionized water at 4° C. For comparative purposes, a commercial protease, Enzeco ® was dialyzed against deionized water as the GX6644 protease.

The proteases were incubated at a concentration of 400 ADU/ml in 0.15% STPP buffer adjusted from pH 6 to pH 12.0 (The concentration of STPP is the usual concentration in detergent suds). The enzyme-buffer solutions were incubated at 25° C. for 24 hours under these conditions. The pH of each solution was determined after enzyme addition with a Beckman pHI 40 pH meter calibrated at 25° C. After the 24 hour incubation period, the residual protease activity was determined at pH 10.0 (0.4% STPP buffer) using the Delft assay (Relative residual activity obtained with the peptidase assay was identical). The results demonstrating higher alkaline stability of GX6644 protease is demonstrated in the following tables:

| | GX6644 | | | | | | | | | |
|---|---|---|---|---|---|---|---|---|---|---|
| Measured pH | 6.1 | 7.5 | 8.2 | 8.5 | 8.9 | 9.1 | 9.6 | 10.3 | 10.5 | 11 |
| Residual activity (%) | 92 | 93 | 97 | 98 | 100 | 95 | 94 | 87 | 57 | 16 |
| | Enzeco ® | | | | | | | | | |
| Measured pH | 6.3 | 7.2 | 8.2 | 9.1 | 9.3 | 10.1 | 10.7 | 11.1 | | |
| Residual activity (%) | 100 | 99 | 59 | 16 | 13 | 1 | 4 | 16 | | |

EXAMPLE 4

Washing tests were performed in a Tergotometer using EMPA-116 (Enzyme Manufacturers Performance Assay from Test Fabrics, Inc., N.Y., N.Y.) as a test fabric. Commercial detergents (0.5 g/l) were added to 1 liter of water with a hardness of 30 mg/l CaCO$_3$ plus 60 mg/l MgSO$_4$. Three 6" by 6" pieces of EMPA-116 were added subsequent to the addition of 2,000 ADU of GX6644 protease. The wash was performed for 15 mintues at 75 rpm agitation at various temperatures. After decanting the wash water, the fabrics were rinsed twice with 1-liter each of cold tap water, lightly ironed and dried. Reflectances of swatches were determined with a Gardner Colorimeter (giving ΔL values) and compared to EMPA-116 swatches that were washed under identical conditions except enzyme was omitted. Reflectance was read on both sides of each cloth, a total of 10 readings per cloth. The results are expressed as the mean of 30 ΔL (3 EMPA-116 fabrics) readings for each test.

The results of using GX6644 protease in the nonphosphate based, U.S. heavy duty liquid detergent Wisk ® (Lever Bros. Co., Inc., N.Y., N.Y.) is as follows:

| Addition | Temperature (°C.) | Δ L | % Increase in Cleaning |
|---|---|---|---|
| None | 22 | 4.09 | — |
| GX6644 Protease | 22 | 5.97 | 46 |
| None | 38 | 6.10 | — |
| GX6644 Protease | 38 | 8.94 | 47 |

The results of supplementing a phosphate-based, heavy-duty laundry powder (Fresh Start ® base [containing no enzymes] obtained from Colgate-Palmolive, Co., Inc., N.Y., N.Y.) are shown in the following table:

| Addition | Temperature (°C.) | Δ L | % Increase in Cleaning |
|---|---|---|---|
| None | 38 | 25.53 | — |
| GX6644 protease | 38 | 28.69 | 12 |
| None | 50 | 24.08 | — |
| GX6644 protease | 50 | 26.63 | 11 |

The tables show that GX6644 protease is suitable for addition to washing compositions for enhanced washing ability. Furthermore, the results demonstrate the efficacy for using GX6644 protease to improve washing during cold (22° C.), warm (38° C.) and hot water (50° C.) washings.

We claim:

1. A process for the preparation of an enzyme having high proteolytic activity in alkaline media and exhibiting high alkaline stability which comprises cultivating Bacillus strain GX6644 or an alkaline protease producing mutant or variant thereof in a fermentation medium and recovering therefrom the enzyme produced by said Bacillus strain.

2. The process of claim 1, wherein the fermentation medium comprises carbon, nitrogen, magnesium salts, calcium salts and trace elements.

3. The process of claim 1, wherein following cultivation of the Bacillus strain the fermentation medium is centrifuged to remove cellular material, then the enzyme is concentrated in the supernatant, precipitated from said supernatant and recovered.

4. A member of the group consisting of Bacillus novel species GX6644 and its alkaline protease producing mutants and variants.

5. A biologically pure culture of Bacillus strain GX6644 or an alkaline protease producing mutant or variant thereof.

6. A substantially pure alkaline protease characterized by the following properties:
   (a) a molecular weight of about 26,500;
   (b) an isoelectric point of about 9.5;
   (c) an optimal proteolytic activity at a pH of about 11.0 at a temperature of 40° C., said optimal activity measured by the Delft method using 0.4% STPP as buffer and casein as substrate;
   (d) an optimal activity at 45°–50° C. at a pH of 8.5 or 10.0, said optimal activity measured by the Delft method using casein as substrate;
   (e) an amino acid composition of:

| amino acid | GX6644 |
|---|---|
| LYS | 4 |
| HIS | 5 |
| ARG | 8 |
| ASP | 31 |
| THR | 13 |
| SER | 16 |
| GLU | 15 |
| PRO | 9 |
| GLY | 39 |
| ALA | 39 |
| CYS | 0 |
| VAL | 26 |
| MET | 5 |
| ILE | 11 |
| LEU | 13 |
| TYR | 4 |
| PHE | 5; |

(f) distinct immunological cross-reactivity as determined by the Ouchterlony double diffusion method; and
   (g) an $NH_2$-terminus of glutamine.

7. A washing composition containing an effective amount of the enzyme of claim 6 having high alkaline stability.

8. The washing composition of claim 7 which further comprises a detergent.

9. The washing composition of claim 8, which further comprises one or more components selected from the group consisting of a detergent builder, foam booster, fragrance and coloring agent.

10. The washing composition of claim 8, wherein said detergent is selected from the group consisting of an ethoxylated alcohol and a linear alkyl sulfonate.

11. The washing composition of claim 9 wherein the detergent builder is nitriloacetate, trisodium salt.

* * * * *